US008934686B2

(12) United States Patent
Ostrovsky-Berman et al.

(10) Patent No.: US 8,934,686 B2
(45) Date of Patent: Jan. 13, 2015

(54) USER INTERFACE FOR SELECTING PATHS IN AN IMAGE

(75) Inventors: Yaron Ostrovsky-Berman, Petach-Tikva (IL); Hadar Porat, Tel-Aviv (IL); Oranit Dror, Rishon-LeZion (IL); Tiferet Ahavah Gazit, Tel-Aviv (IL); Michael Slutsky, Kfar-Saba (IL)

(73) Assignee: Algotec Systems Ltd., RaAnana (IL)

( * ) Notice: Subject to any disclaimer, the term of this patent is extended or adjusted under 35 U.S.C. 154(b) by 1023 days.

(21) Appl. No.: 12/953,491

(22) Filed: Nov. 24, 2010

(65) Prior Publication Data
US 2011/0135175 A1 Jun. 9, 2011

Related U.S. Application Data (60) Provisional application No. 61/264,676, filed on Nov. 26, 2009.

(51) Int. Cl.
G06K 9/00 (2006.01)
G06F 19/00 (2011.01)

(52) U.S. Cl.
CPC .................................. G06F 19/321 (2013.01)
USPC ............ 382/128; 382/131; 382/295; 600/410

(58) Field of Classification Search
USPC .......... 382/128–131, 260, 266, 295; 378/4, 8, 378/41; 600/407–429, 431, 443; 345/420
See application file for complete search history.

(56) References Cited

U.S. PATENT DOCUMENTS

| 6,501,848 | B1 | 12/2002 | Carroll et al. | |
|---|---|---|---|---|
| 6,845,260 | B2 | 1/2005 | Liu et al. | |
| 7,003,144 | B2 | 2/2006 | Yim | |
| 7,043,064 | B2 * | 5/2006 | Paik et al. | 382/128 |
| 7,113,623 | B2 | 9/2006 | Chen et al. | |
| 7,369,691 | B2 | 5/2008 | Kondo et al. | |
| 7,397,937 | B2 * | 7/2008 | Schneider et al. | 382/130 |
| 7,480,258 | B1 * | 1/2009 | Shuen et al. | 370/256 |
| 7,953,266 | B2 * | 5/2011 | Gulsun et al. | 382/131 |
| 7,970,189 | B2 * | 6/2011 | Buelow et al. | 382/128 |
| 2002/0164060 | A1 * | 11/2002 | Paik et al. | 382/128 |
| 2002/0164061 | A1 * | 11/2002 | Paik et al. | 382/131 |
| 2002/0176635 | A1 * | 11/2002 | Aliaga et al. | 382/284 |

(Continued)

OTHER PUBLICATIONS

Philips "Computed Tomography: Comprehensive Cardiac Analysis", Koninklijke Philips Electronics, Brochure, 6 P., Oct. 2005.

(Continued)

Primary Examiner — Chan Park
Assistant Examiner — Mia M Thomas (57) ABSTRACT

A method, performed by a computer, of facilitating selection by a user of one path from a set of directed paths in an image, partly overlapping but not constituting a directed tree structure, each path beginning at a root and ending at an end point, the method comprising:
 a) receiving from the user an indication of a specified location in the image;
 b) identifying a specified path part that best matches the indication of the specified location; and
 c) suggesting primarily a single path chosen from among two or more paths in the set which include the specified path part, but do not all follow a same route before the specified path part, and at least one of which separates from another path somewhere along its length.

29 Claims, 3 Drawing Sheets

(56) References Cited

U.S. PATENT DOCUMENTS

| | | | |
|---|---|---|---|
| 2003/0185426 A1* | 10/2003 | Ohishi | 382/128 |
| 2004/0077941 A1* | 4/2004 | Reddy et al. | 600/428 |
| 2004/0086175 A1* | 5/2004 | Parker et al. | 382/154 |
| 2004/0215073 A1* | 10/2004 | Vilsmeier et al. | 600/407 |
| 2005/0018058 A1* | 1/2005 | Aliaga et al. | 348/239 |
| 2005/0058330 A1* | 3/2005 | Mitsuhashi et al. | 382/128 |
| 2005/0286739 A1* | 12/2005 | Pilu | 382/103 |
| 2006/0178825 A1* | 8/2006 | Eglington et al. | 701/211 |
| 2006/0251304 A1* | 11/2006 | Florin et al. | 382/128 |
| 2006/0251325 A1* | 11/2006 | Florin et al. | 382/173 |
| 2007/0016016 A1* | 1/2007 | Haras et al. | 600/431 |
| 2007/0024617 A1* | 2/2007 | Poole | 345/424 |
| 2007/0116332 A1* | 5/2007 | Cai et al. | 382/128 |
| 2007/0160274 A1* | 7/2007 | Mashiach | 382/128 |
| 2007/0165917 A1* | 7/2007 | Cao et al. | 382/128 |
| 2007/0217665 A1* | 9/2007 | Kiraly et al. | 382/128 |
| 2007/0263915 A1* | 11/2007 | Mashiach | 382/130 |
| 2008/0097200 A1* | 4/2008 | Blume et al. | 600/431 |
| 2008/0124112 A1* | 5/2008 | Soma et al. | 399/71 |
| 2008/0187199 A1* | 8/2008 | Gulsun et al. | 382/131 |
| 2008/0205728 A1 | 8/2008 | Quist | |
| 2008/0249660 A1* | 10/2008 | Nakamura | 700/250 |
| 2009/0034816 A1* | 2/2009 | Ghanem et al. | 382/131 |
| 2009/0264914 A1* | 10/2009 | Riina et al. | 606/191 |
| 2010/0040200 A1* | 2/2010 | Ema et al. | 378/98.12 |
| 2010/0128940 A1* | 5/2010 | Buelow et al. | 382/128 |
| 2010/0241289 A1* | 9/2010 | Sandberg | 701/2 |
| 2010/0296709 A1* | 11/2010 | Ostrovsky-Berman et al. | 382/128 |
| 2011/0052028 A1* | 3/2011 | Shreiber | 382/131 |
| 2011/0301454 A1* | 12/2011 | Chono | 600/425 |

OTHER PUBLICATIONS

Vital "CT Cardiac Automatic", ViTALCardia, Vital Images, Inc., Brochure, 6 P.

* cited by examiner

USER INTERFACE FOR SELECTING PATHS IN AN IMAGE

RELATED APPLICATION/S

This application claims the benefit of priority under 35 USC 119(e) of U.S. Provisional Patent Application No. 61/264,676 filed Nov. 26, 2009, the contents of which are incorporated herein by reference in their entirety.

FIELD AND BACKGROUND OF THE INVENTION

The present invention, in some embodiments thereof, relates to a method for facilitating a user selecting paths in an image and, more particularly, but not exclusively, to a method for facilitating the selection of particular blood vessels in a 3-D medical image showing one or more networks of blood vessels.

It is difficult to design methods that automatically segment blood vessels, and other connected networks in the body, with acceptably low rates of error. But having a human expert identify each blood vessel voxel by voxel would be impossibly time consuming. Methods that allow a human expert to interact effectively with a display of a medical image, to quickly identify particular blood vessels, could allow accurate segmentation to be achieved in a reasonable time.

The Vitrea Workstation made by Vital Images, and the Advantage Workstation made by General Electric, both include software that automatically finds major coronary arteries, as well as providing semi-automatic and manual tools for finding other arteries.

The Philips Brilliance Workstation includes a Comprehensive Cardiac Analysis application, which allows a user to hover a mouse on a 3D image, to indicate a particular blood vessel in a tree graph of coronary blood vessels, and to accept a suggestion for its path.

U.S. Pat. No. 7,369,691 to Kondo et al describes software that finds centerlines of blood vessels in a 3D image, which can be corrected by a user.

U.S. Pat. No. 6,501,848 to Carroll et al describes a computer reconstruction of a coronary vascular tree. A user can select two points on the image, and the computer then finds a path connecting them through the blood vessels, if one exists, and calculates such parameters as the length, average curvature, and tortuosity of the path.

U.S. Pat. No. 7,113,623 to Chen et al describes software that calculates a moving 3D coronal artery tree, over a cardiac cycle. User input is needed to identify points in the lumen of each artery initially.

U.S. Pat. No. 7,003,144 to Yim describes software that generates a graph of blood vessels from an angiogram. Optionally, the user identifies which points in the graph are distal endpoints of blood vessels, or in some cases the software can figure this out without help from the user.

US2008/0205728 to Quist describes software that generates a tree of pulmonary blood vessels from a CT image, in order to look for a pulmonary embolism, allowing a user to tell at a glance if a large part of the tree is missing.

US2008/0187199 to Gulsun et al describes software in which a user selects a seed that is near the beginning of a blood vessel, and the algorithm finds the centerline and tree structure of the blood vessel.

SUMMARY OF THE INVENTION

An aspect of some embodiments of the invention concerns a user interface for facilitating selection by a user of paths from one or more networks of paths in an image, for example a network of blood vessels, even if the network is not in the form of a tree structure, and/or allows the user to accept part of a suggested path and to indicate how the rest of the path should extend. Both these features may make it easier for a user to rapidly select and identify blood vessels in a network even if there are errors in the topology of the network.

There is thus provided, according to an exemplary embodiment of the invention, a method, performed by a computer, of facilitating selection by a user of one path from a set of directed paths in an image, partly overlapping but not constituting a directed tree structure, each path beginning at a root and ending at an end point, the method comprising:
 a) receiving from the user an indication of a specified location in the image;
 b) identifying a specified path part that best matches the indication of the specified location; and
 c) suggesting primarily a single path chosen from among two or more paths in the set which include the specified path part, but do not all follow a same route before the specified path part, and at least one of which separates from another path somewhere along its length.

Optionally, the method also comprises:
 a) receiving from the user an acceptance of the suggested path as the path to be selected, or a partial or complete rejection of the suggested path;
 b) if a rejection is received, suggesting primarily a single new path chosen from the set of paths or from a changed set of paths, different from the previous suggested path.

Optionally, receiving comprises receiving a complete rejection of the suggested path, and suggesting the new path comprises suggesting, in response to the rejection, a new path that includes a specified path part that best matches a new indication of a specified location in the image, received from the user.

Alternatively, receiving comprises receiving a partial rejection of the suggested path, and suggesting a new path comprises suggesting a new path that, in response to the partial rejection, is chosen to include the same specified path part as the previous suggested path.

Optionally, the new path is chosen from a changed set of paths, and is not included in the original set of paths.

Optionally, the new path is chosen, in response to the partial rejection, to be the same as the previous path from their root up to the specified path part, differing from the previous path only after the specified path part.

Optionally, the method also comprises receiving from the user an indication of an extension portion location in the image, wherein the new path is chosen to have a portion after the specified path part, different from the previous path, that best matches the indicated extension portion location.

Optionally, also comprising receiving an indication from the user of a specified root, and suggesting a path or suggesting a new path, or both, comprises suggesting a path beginning at the specified root.

Optionally, suggesting a path or suggesting a new path, or both, comprises:
 a) evaluating a length of each of a plurality of paths from the specified root to the specified path part; and
 b) giving priority to one or more paths that have shorter said length.

Optionally, the image is a medical image, and the paths in the set of paths correspond to blood vessels in the image.

Optionally, suggesting a path, or suggesting a new path, or both, comprises:

a) for a plurality of paths, evaluating a degree to which the blood vessel corresponding to the path resembles a blood vessel in a category; and b) giving priority to one or more paths corresponding to blood vessels which have a greater degree of resemblance to vessels in said category.

Optionally, suggesting a path, or suggesting a new path, or both, comprises giving higher priority to one or more paths that correspond to more major blood vessels.

Optionally, the paths in the set of directed paths together include at least one loop.

There is further provided, in accordance with an exemplary embodiment of the invention, a method of facilitating the selection by a user of a plurality of paths from a set of directed paths in an image, the method comprising:

a) selecting one path in the image, using the method of an embodiment of the invention, also comprising receiving from the user an acceptance or a partial or complete rejection of each suggested path, and each time a partial or complete rejection is received, suggesting primarily a single new path, chosen from the set of paths or from a changed set of paths, different from the previous path; and b) selecting one or more additional paths using the method of (a), with previously selected paths excluded from the set of paths and from any changed set of paths.

There is further provided, in accordance with an exemplary embodiment of the invention, a method, performed by a computer, of facilitating selection by a user of one path from a set of directed paths in an image, each path beginning at a root and ending at an end point, the method comprising:

a) receiving from the user an indication of a specified location in the image;

b) identifying a specified path part that best matches the specified location;

c) suggesting primarily a single path chosen from among two or more paths in the set which include the specified path part;

d) receiving from the user a partial rejection of the suggested path, with an indication of an extension portion location in the image; and e) suggesting primarily a single new path, chosen, in response to the partial rejection of the previous suggested path, from among paths in the set of paths or in a changed set of paths, to have a portion after the specified path part, different from the previous suggested path, that best matches the indication of the extension portion location.

Optionally, the new path is chosen to have an end point that best matches the indication of the extension portion location.

Optionally, the new path is chosen from among paths that are the same as the previous suggested path from the root to the specified path part, but differs after the specified path part.

Optionally, the new path is the same up to its end point as the previous suggested path, but ends before the previous suggested path ends.

Optionally, the new path is so chosen in response to a request from the user to make the new path like the previous suggested path but truncated at an indicated end location.

Optionally, the new path is chosen from a changed set of paths, and is not in the original set of paths.

Optionally, at least a portion of the new path is not part of any path in the original set of paths.

There is further provided, in accordance with an exemplary embodiment of the invention, a method of facilitating the selection by a user of a plurality of paths from a set of directed paths in an image, the method comprising, for each path to be selected:

a) performing:
   i) receiving from the user an indication of a specified location in the image;
   ii) identifying a specified path part that best matches the specified location;
   iii) suggesting primarily a single path chosen from among two or more paths in the set which include the specified path part;

b) receiving from the user an acceptance, a partial rejection, or a complete rejection of the suggested path, as the path to be selected;

c) if a complete rejection is received, performing (a) again, and if a partial rejection is received, receiving from the user an indication of a new end location and suggesting primarily a single new path, chosen, in response to the partial rejection of the previous suggested path, from among paths in the set of paths or in a changed set of paths, to have a portion after the specified path part, different from the previous suggested path, that best matches the indication of the extension portion location; and d) repeating (b) and (c) until an acceptance of the suggested path is received; wherein a partial rejection is received for at least one suggested path.

There is further provided, according to an exemplary embodiment of the invention, a method of facilitating the selection by a user of a plurality of paths from a set of directed paths in an image, the method comprising selecting one or more paths in the image by successively suggesting only one path at a time from the set of paths or from a changed set of paths, and each time receiving from the user an acceptance or a partial or complete rejection of each path as the path to be selected, until an acceptance is received, wherein previously selected paths are excluded from the set of paths and from any changed set of paths, and selecting at least one of the paths is done according to the method described immediately above.

There is further provided, in accordance with an exemplary embodiment of the invention, a computer with access to image data, comprising:

a) a monitor for displaying images from the image data;

b) a user input device for indicating a location in the displayed image, and for receiving instructions from a user; and c) a CPU programmed to perform the method of claim 1 or claim 15 to facilitate selection by the user of one path from a set of directed paths in the image, using the monitor and the input device to receive the indication of the specified location in the image.

Optionally, the computer also comprises enough memory to perform the method according to an exemplary embodiment of the invention, for the network of coronary arteries in a human heart.

Optionally, the computer is programmed to run segmentation software for coronary arteries of the human heart, wherein the CPU is fast enough, and the memory is big enough, to run both the segmentation software and to perform the method of exemplary embodiment of the invention.

Optionally, the computer has no more than 4 megabytes of memory.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

Implementation of the method and/or system of embodiments of the invention can involve performing or completing selected tasks manually, automatically, or a combination thereof. Moreover, according to actual instrumentation and equipment of embodiments of the method and/or system of the invention, several selected tasks could be implemented by hardware, by software or by firmware or by a combination thereof using an operating system.

For example, hardware for performing selected tasks according to embodiments of the invention could be implemented as a chip or a circuit. As software, selected tasks according to embodiments of the invention could be implemented as a plurality of software instructions being executed by a computer using any suitable operating system. In an exemplary embodiment of the invention, one or more tasks according to exemplary embodiments of method and/or system as described herein are performed by a data processor, such as a computing platform for executing a plurality of instructions. Optionally, the data processor includes a volatile memory for storing instructions and/or data and/or a non-volatile storage, for example, a magnetic hard-disk and/or removable media, for storing instructions and/or data. Optionally, a network connection is provided as well. A display and/or a user input device such as a keyboard or mouse are optionally provided as well.

BRIEF DESCRIPTION OF THE DRAWINGS

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings.

DESCRIPTION OF EMBODIMENTS OF THE INVENTION

The present invention, in some embodiments thereof, relates to a method for facilitating a user selecting paths in an image and, more particularly, but not exclusively, to a method for facilitating the selection of particular blood vessels in a medical image showing one or more networks of blood vessels.

An aspect of some exemplary embodiments of the invention concerns a method, implemented on a computer, for facilitating selection by a user of directed paths in an image, for example blood vessels in a medical image. The paths partly overlap, but do not constitute a directed tree structure, because, for example, they may contain loops, and/or multiple starting points as well as multiple end points, and/or two paths may point in opposite directions in a portion where they overlap. In a directed tree structure, all paths would be directed away from a single root of the tree, or else all paths would be directed toward the root. This non-tree structure may reflect the actual topology of blood vessels in the image, for example there may be a bypass in an image of coronary arteries, and it may also reflect errors in segmenting the blood vessels which lead to incorrect connections between them. The method comprises making suggestions of particular paths that meet certain criteria indicated by the user, which may be accepted or rejected by the user. Optionally, the method includes making changes in the paths, for example attempting to correct errors in their connections, if one or more suggested paths are rejected by the user. Corrections to the paths may also be made by the user. Optionally, the user can accept part of a path, and indicate a different way to extend the path beyond the part that was accepted, or a point for truncating the path. The method provides an easy, intuitive way for a user to find a particular path, even in the presence of non-tree structures such as loops, and even in the presence of the kinds of errors in the topology of the paths that often arise in segmentation of blood vessels, for example.

An aspect of some embodiments of the invention concerns a method, implemented on a computer, for facilitating selection by a user of directed paths in an image, in which particular paths are suggested to the user, who may accept them, or partially or completely reject them. If a path is partially rejected, then an initial part of the path is accepted, and the user indicates a location in the image where the path should extend to, or a location where the path should be truncated. This may allow the user to rapidly zero in on a desired path, in an intuitive way, in spite of errors in the list of paths, for example topological errors in the way a network of blood vessels is represented, and even if the paths do not form a directed tree structure. Optionally, if the user rejects one or more suggested paths, changes are made in the list of paths, for example changing the way they are connected to each other. These changes may be made automatically, or by the user. The changes may correct errors in the set of paths, allowing the user to find the path that is sought.

Optionally, once a path is accepted by a user, it is excluded from suggested paths offered to the user when selecting other paths. In the case of a network of blood vessels in a medical image, the method may be used by the user, for example, to select and identify various named blood vessels that appear in the image.

Suggested paths may be offered to the user, one at a time, in response to an indication by the user of a location in the image of a part of the path. If there is more than one path that includes that part, the decision as to which path to suggest first may be random, or it may depend on such criteria as the length of the path, and whether it appears to have characteristics of a desired category of paths, for example either arteries or veins, depending on which one is sought, in the case where the paths follow blood vessels.

Optionally, the method is performed as a user interface, as part of a process that includes using segmentation software to segment the image before running the user interface. Optionally, the whole process is performed using a single computer, which is optionally a personal computer, such as radiologist might have in his office or home, rather than a high-end workstation associated with an imaging system such as a CT system or an MRI system. However, the computer could obtain imaging data remotely from a server associated with the imaging system. Optionally, medical diagnostic software, using the results of the user interface as input, is also run as part of the process, optionally on the same computer.

Before explaining at least one embodiment of the invention in detail, it is to be understood that the invention is not necessarily limited in its application to the details set forth in the following description. The invention is capable of other embodiments or of being practiced or carried out in various ways.

Figure 1:
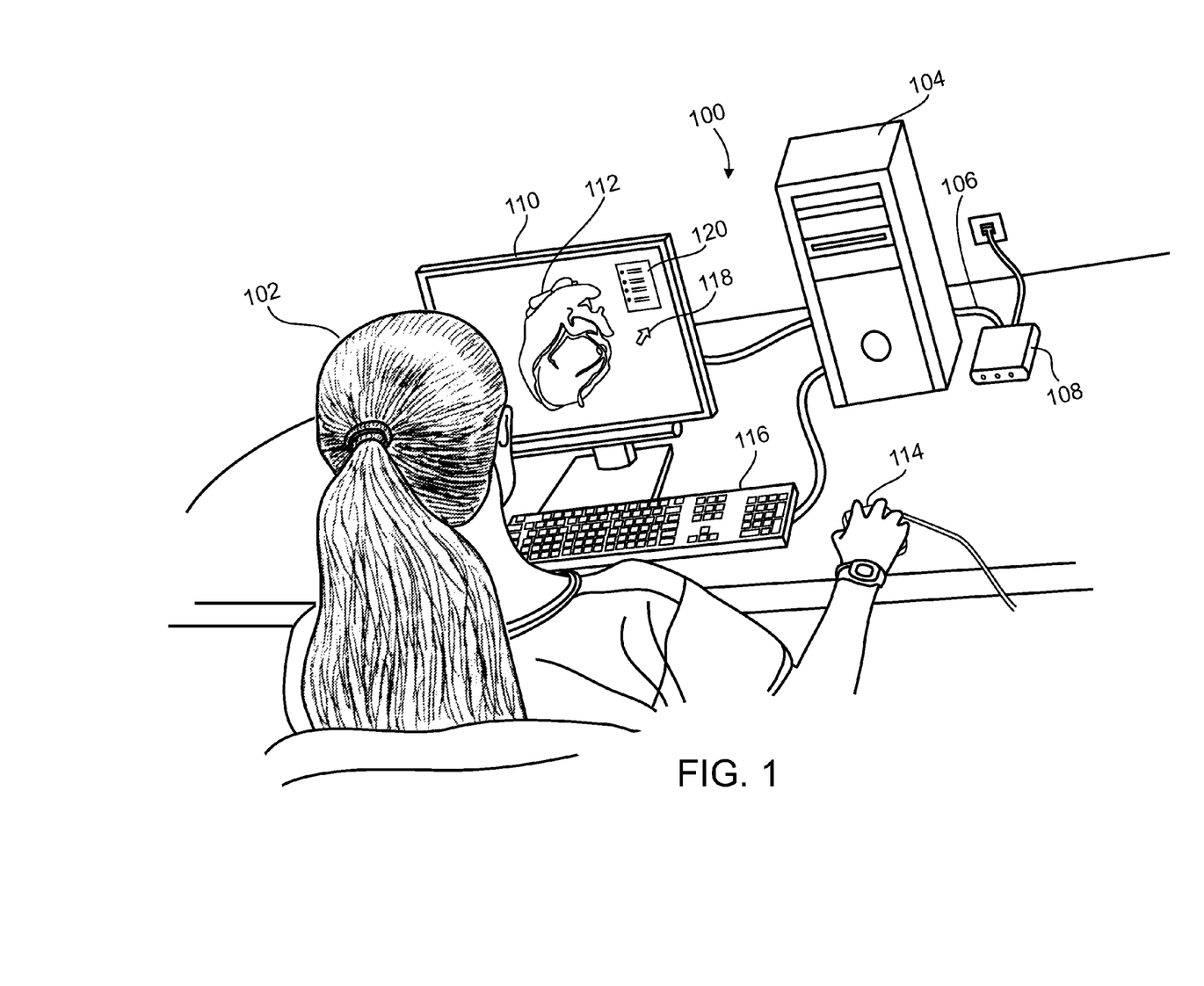
FIG. 1 schematically shows a user using a user interface to select blood vessels in a medical image, according to an exemplary embodiment of the invention.

Referring now to the drawings, FIG. 1 illustrates a system 100 for selecting blood vessels in a medical image, by a user 102. Software implementing this user interface runs, for example, on a computer 104. The computer optionally obtains data of a medical image, for example a three dimensional CT or MRI image of blood vessels. The method can also be used for other biological networks and branching structures, such as lymph vessels, air passages in the lungs, and nerves. Although the computer may itself be a high powered work station associated with an imaging system, it may also be a picture archiving and communication system (PACS), such as a relatively low powered personal computer which obtains the imaging data remotely from a server connected to a database, and runs the user interface software locally. The imaging data is obtained, for example, through a cable 106 connected to a modem 108.

Optionally, computer 104 also runs segmentation software that processes the imaging data, before the user interface software is run. It may be advantageous to run the segmentation software and the user interface locally on the same computer, particularly if this can be done on a mid-range desktop computer so that every radiologist can run the segmentation software and user interface on his own computer, downloading only the imaging data from a server associated with the imaging system. Suitable segmentation software for this purpose, in the case of identifying blood vessels, is described in two provisional U.S. patent applications, with Ser. Nos. 61/179,386 and 61/179,783, filed on May 19, 2009 and May 20, 2009, respectively titled, "Method and System for Blood Vessel Segmentation and Classification" and "Soft Tissue Segmentation Using a Bone Atlas." The first of these applications specifically describes segmentation algorithms suitable for coronary arteries that include loops. The inventors have found that a personal computer with no more than 4 megabytes of memory is adequate to run such segmentation software and the user interface.

A monitor 110 displays a medical image 112, for example an image of the heart in which blood vessels have been identified by automatic segmentation software. In the case of a heart image, the segmentation software also optionally removes the rib cage and lungs from the image, so that blood vessels on the surface of the heart are visible. Associated with the image is data on a set of paths, corresponding for example to the centerlines of the blood vessels, found by the segmentation software. The blood vessels may be tentatively identified in the set of paths as arteries and veins. The set of paths may be missing some path segments that should be present, and it may include some spurious path segments that should not be present, based on the actual connections of the corresponding blood vessels. The data for the set may also have some artery segments misidentified as vein segments, and vice versa. User 102 uses an input device, such as a mouse 114 and/or a keyboard 116, to enter data, for example by moving around a cursor 118, and/or by selecting an item from a menu 120. Using the mouse and the cursor, for example, the user indicates a location on the screen, in order to indicate a part of a path, while a drop-down menu may be used, for example, to accept or reject a suggested path, as will be explained below.

Figure 2:
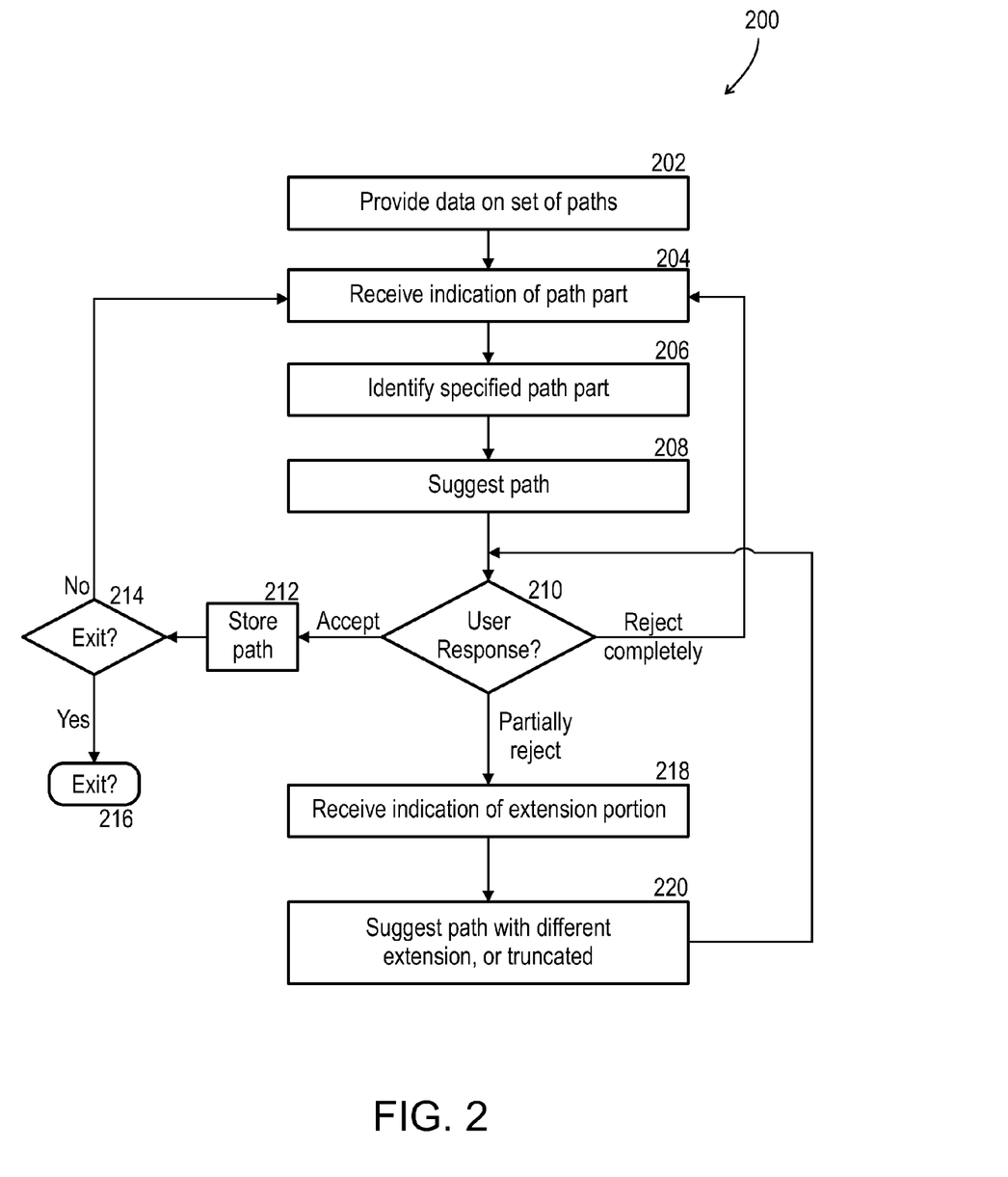
FIG. 2 is a flow diagram of a user interface for selecting paths in an image, according to an exemplary embodiment of the invention.

FIG. 2 shows a flowchart 200 for a user interface which allows a user to select a desired path from a set of directed paths in an image. Data on the set of paths is provided at 202, for example by automatic segmenting software using the image as input. The data may be generated locally from the image, or it may be generated once and stored with the image archivally. The data includes such information as the location in the image, typically a three-dimensional location, of the root (starting point) and end point of each path, as well as data describing the location of the intermediate points on the path. This could be provided, for example, in the form of a list of coordinates for points closely spaced along the path, in order, from the root to the end point. The paths partially overlap, with some path segments in space belonging to more than one path. Two paths that are initially following a same segment may separate from each other at a branch point, and two paths that are initially separate may later join together at a branch point.

It should be understood that terms such as "initially," "later," "earlier," "before," "after," "begin," "end," "join," and "separate," when used herein in reference to the directed paths, are metaphors that treat the direction of the path as if it were an arrow of time from the past to the future. So, for example, saying that a path begins at a root and ends at an end point means that the path goes between the root and the end point, with the direction of the path pointing from the root to the end point. Saying that two paths separate from each other means that, when travelling along one of the paths in the path direction, one will initially be travelling along a portion where both paths follow the same route, followed by a portion where they follow different routes. When the paths represent a category of blood vessels, for example arteries or veins, the path direction may be generally in a direction from the thicker blood vessels to the thinner blood vessels, which is in the direction of blood flow for arteries, and opposite to the direction of blood flow for veins. However, this need not always be true, and in some cases, two paths may be directed in opposite directions along the same blood vessel, for example if there is some doubt as to its identification as an artery or vein, or as to the direction of blood flow.

At 204, an indication of the location of a path part is received from the user, for example when the user moves a cursor to the location in the image of the path part with the mouse, or clicks on that location. The path part may be a segment of a path, or a critical point on a path, for example an end point or a branching point. Using a segment of the path, rather than a critical point, has the potential advantage that there is a broader range of locations in the image over which the segment passes, so it may be possible to choose a relatively uncrowded location in the image to move the cursor to, to indicate the segment unambiguously. A critical point, on the other hand, may happen to be located near critical points of other paths, either in three dimensional space or in a two-dimensional projection used for indicating the location of the path part, so it may be more difficult for the software to tell which point is intended.

At 206, the software identifies a specified path part, for example a segment in the image along which one or more paths pass, that best matches the indication of the path part received from the user. For example, the specified path part may be the path segment that passes closest, in the image displayed on the monitor, to the point in the display on which the user moved the cursor. Preference may also be given to a path segment that is further to the front in the image, if there is more than one path segment that is close to the point in the display where the user moved the cursor. Optionally, if no path part is within a certain distance from the cursor, optionally controllable by the user, then no specified path part is identified. Optionally, the image displayed on the monitor may be a two dimensional perspective view of a three dimensional image, for example a volume rendered image or a maximum intensity projection image. Alternatively, it may be a two dimensional slice of a three dimensional image. Using a perspective view has the potential advantage that it may be more intuitive for a user to locate a particular blood vessel of interest on it. Using a slice has the potential advantage that there is no ambiguity as to which point in three dimensional space was intended, and furthermore it should be noted that radiologists and other imaging experts are often accustomed to viewing slices of three dimensional images, and interpreting them.

The specified path part identified at 206 need not be the path that passes closest to the point indicated by the user in the display. If some paths have already been selected by the user, then those paths are optionally excluded, in considering how to identify the specified path part. If two different path segments are both fairly close to the point in the image indicated by the user, then other criteria may be used to decide which one to use. For example, if the image is a perspective view, then the path segment that is closest to the viewer may be chosen, and if it is desired to indicate instead a path segment that is behind it, then the image may be rotated, bringing that path segment to the front. Additionally or alternatively, preference may be given to path segments that belong to more major blood vessels, or to path segments that appear to be a particular category of path, for example arteries, or to path segments whose validity is more certain. Optionally, the user specifies that the paths should be limited to paths coming from a particular specified root. For example, if only cardiac arteries are of interest, the specified root could be a point in the aorta to which all of the cardiac arteries can be traced back.

At 208, the software suggests primarily a single path to the user. This may be done, for example, by showing the path on the monitor display in a bright color, or in a color that contrasts with the rest of the image. Saying that the software suggests primarily a single path to the user does not exclude the possibility that one or more other paths are offered to the user at the same time as secondary alternatives, but means that a single path is pointed out or highlighted as the primary path to be considered by the user at that time for acceptance or rejection. Optionally, if there is more than one image displayed, for example from different perspectives, or a perspective view and a slice view, the path is displayed on more than one of them, or on all of them. In general, there may be more than one path that at least partly follows the specified path part, so there may be more than one path that can be suggested, and various criteria may be used to decide which path to suggest first. Some possible criteria will be illustrated using FIGS. 3A-3C, which show different types of situations that may arise. In some embodiments of the invention, instead of suggesting only a single path, the list of possible paths that include the specified path part is narrowed down to a selection of two of more paths for the user to choose between.

Figure 3A:
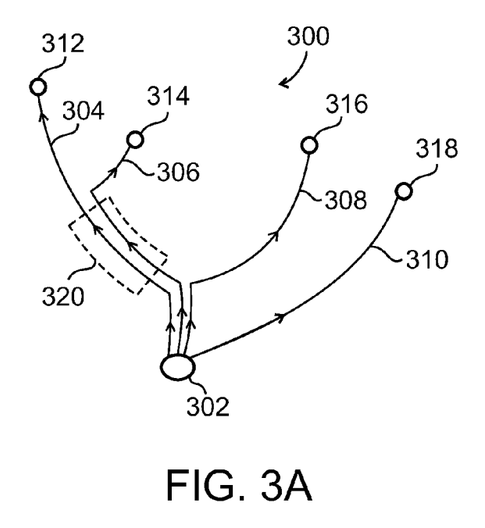
FIGS. 3A-3C schematically shows different configurations of paths that might occur in a network of paths used in the method of FIG. 2, for example.

FIG. 3A shows a set 300 of directed paths, all beginning at root 302. Path 306 goes off to the left. Path 306 follows path 304 for some distance, illustrated schematically in FIG. 3A by showing the two paths parallel to each other and closely spaced. Path 306 then separates from 304, moving off in a different direction. Path 308 separates from paths 304 and 306 earlier than they separate from each other, and path 310 separates from the other paths at root 302. Paths 304, 306, 308 and 310, end respectively at end points 312, 314, 316, and 318. This situation arises when the paths follow arteries, for example, which have a tree structure, branching apart but not coming together again.

If the user indicates path part 320, a path segment that includes both path 304 and path 306, then either path might be suggested. Optionally, the choice is made at random. Alternatively, one or more features of the paths are used to decide. For example, the fact that path 304 extends further than path 306 from the point where they separate, may mean that path 304 is a more major blood vessel, more likely to be the one intended by the user, so optionally it is suggested first, or at least given higher priority. Alternatively or additionally, higher priority is given to one or more paths following blood vessels that appears more likely to be an artery, if arteries are being selected, according to various criteria used by the segmentation software. Alternatively or additionally, higher priority is given to one or more paths following more major blood vessels, as identified, for example, by the segmentation software.

It should be understood that if more than one feature of the paths is used to assign priority, then the path that gets highest priority according to one feature will not necessarily be the first path suggested. The priorities assigned according to the different features may be combined by averaging them in some way, or one feature may be used first, and other features only used if the first feature shows no clear preference.

Because of the tree structure in FIG. 3A, there is no ambiguity as to how the paths should be traced back to the root.

Figure 3B:
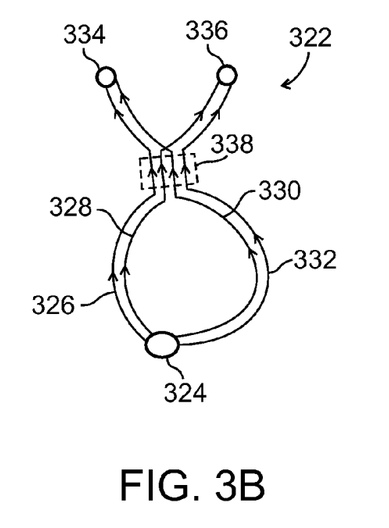

FIG. 3B illustrates another set 322 of directed paths, which do not have a tree structure. In this case, two blood vessels diverge from a root 324, but then come together again, forming a loop, before splitting apart again into two blood vessels. Such a situation could occur, for example, in coronary arteries in a patient who has had coronary by-pass surgery, or in cerebral arteries in any person, due to the circle of Willis. There are four possible paths in set 322. Paths 326 and 328 follow the blood vessel going off to the left from the root, while paths 330 and 332 follow the blood vessel going off the right. When the two vessels come together and split apart again, paths 326 and 330 follow the blood vessel that ends at end point 334, while paths 328 and 332 follow the blood vessel that ends at end point 336. If the user indicates path segment 338 as the specified path part, then any one of these four paths could be suggested first.

Optionally, the choice between paths 326 and 330 on the one hand, and paths 328 and 332 on the other hand, is made according to any of the criteria described for choosing between path 304 and 306 in FIG. 3A. These criteria are optionally used whenever deciding between two paths which diverge after the specified path part. For example, because the blood vessel on the left, ending at end point 334, is longer than the vessel on the right, ending at end point 336, paths 326 and 330 could be suggested before paths 328 and 332.

The choice between paths 326 and 328 on the one end, and paths 330 and 332 on the other hand, is optionally made by different criteria, which are optionally used whenever deciding between two paths that separate and then join together again. For example, the most direct (shortest) path from root 324 to the point where the two blood vessels come together again, is optionally suggested first, or given higher priority, because it may be less likely to be a mistake, and it may be more likely than the longer paths to be following an original blood vessel in the case of a by-pass patient. Additionally or alternatively, if the blood vessels to be selected are arteries, then the path is picked which appears to more closely resemble an artery, according to various criteria used by the segmentation software. The other path may be more likely to be following a vein that was mistakenly identified as an artery by the segmentation software. A path that has been identified by the segmentation software as following a more major blood vessel may also be given higher priority.

As in FIG. 3A, if more than one criterion is used in deciding which path to suggest first, then the priorities from the different criteria may be combined or averaged in some way, or one criterion may take precedence, and the other criteria only used if the first criterion does not result in a clear preference.

It should be noted that if the imaging field of view for set 332 did not include root 324, then paths 326 and 328 would appear to have a different starting point than paths 330 and 332. In that case, any of the criteria suggested above for deciding which path to suggest first could still be used. However, it might not be very meaningful to compare the lengths of the paths in this case, since they may depend to a considerable extent on the position of the edge of the imaging field of view, rather than on properties of the blood vessels themselves.

Figure 3C:
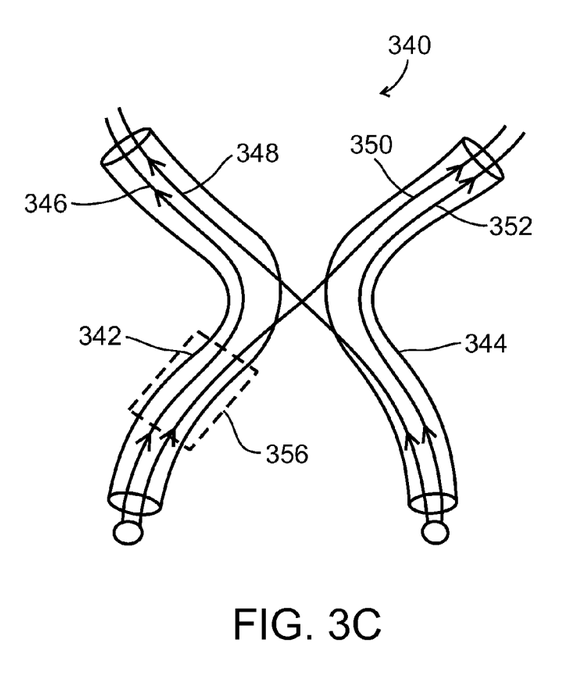

FIG. 3C shows a set 340 of directed paths. Two blood vessels 342 and 344 start out at different places, come close together, and move apart, without actually joining, and they respectively have paths 346 and 352. However, because the vessels come so close together, it looks to the segmentation software as if they are joined together over a short distance. As a result, two spurious paths are included in the set, path 350 which crosses over from vessel 342 to vessel 344, and path 348 which crosses over from vessel 344 to vessel 342. It might also happen that the segmentation software would not think that the two blood vessels joined together, but would incorrectly think that the top part of vessel 342 is joined to the bottom part of vessel 344, and the top part of vessel 344 is joined to the bottom part of vessel 342. In this case, only the spurious paths 348 and 350 would be included in the set of paths, and not the real paths 346 and 352.

In order to overcome such errors in the segmentation software, the set of directed paths can optionally be changed, before suggesting a path, possibly to eliminate spurious paths, but more importantly, to add genuine paths that are missing. For example, whenever two paths are less than a certain distance apart, new path segments connecting them are optionally added, and corresponding new paths are added to the set, to be considered as suggested paths. Optionally, this is done when the data on the set is provided at 202. Alternatively, it is not done until, as will be described below, other paths have been suggested and rejected, optionally all other paths in the set that include the specified path part. For example, if path part 356 is indicated by the user, and paths 346 and 352 are not included because of an error in the segmentation software, then only spurious path 350 will be suggested as a path. Optionally, the set of paths is changed only after path 350 is rejected by the user, and there is no other choice to suggest in the present set of paths.

The set of paths may also be changed manually, for example there may be a menu option allowing the user to indicate that a connection should be added between two points in the image that are not already connected, or not already directly connected.

Changing the set of paths adaptively, only as needed, has the potential advantage that errors in the segmentation software can generally be ignored, unless they affect the path that the user is trying to select, and only then are they corrected.

Returning to FIG. 2, at 210 the user responds to the suggested path, accepting it completely, or rejecting it completely, or partly rejecting it.

If the path is accepted, then information about the path, at least the fact that it was accepted, is optionally stored in volatile memory of the computer, or in a permanent storage device such as a hard drive, at 212. Other information that could be stored is the name of a blood vessel that corresponds to the path, as identified by the user. Optionally, all previously accepted paths are shown in the image displayed on the monitor, but for example in a different color or brightness than the paths being suggested. Displaying previously accepted paths in this way has the potential advantage that it could remind the user that those paths have already been found and accepted, and there is no need to find them again. Optionally, accepting a path can also be used to store the latest suggested path in memory, for example if the user wants to end the session, allowing the user to continue the session again later, starting with that path, and possibly rejecting it partly or completely at that time.

Optionally some paths, for example corresponding to major blood vessels that can be reliably found by the segmentation software, are accepted automatically, before the user interface begins operating, and are displayed on the image, for example, in the same color as the other previously accepted paths. Like the other previously accepted paths, these paths are optionally excluded from the paths offered as suggestions in the user interface.

If the path is accepted, then at 214 a decision is made whether to exit the software, at 216. If not, then optionally a new indication of a path part is received from the user at 204, to begin the process for selecting a different path. Optionally, the accepted path is excluded from the set of paths in the future, when suggesting a path. If the suggested path is rejected completely, then optionally a new indication of a path part is also received from the user, at 204. Optionally, rejecting a path completely is done simply by moving the mouse off the indicated location of the path part. The new location of the mouse, if far enough away, will then be taken as a new indication of a path part, and a new path will be suggested. In this scenario, only if the path is to be accepted by the user, or partially rejected, does the user take positive action, such as clicking or right clicking on the mouse, for example to pull down a menu that provides a choice of acceptance or partial rejection of the suggested path.

If the path is partially rejected, then optionally the path is accepted up to the specified path part, but the software will suggest another extension of the path beyond the specified path part. This is referred to as "extension mode." The accepted part of the path in extension mode, called the active path, is optionally displayed on the image in a different color than the previously accepted paths. Optionally, at 218, an indication of an extension portion of the path is received from the user. For example, the user clicks on a location in the image, corresponding to a part of the new extension that she wants to indicate for the path, and the extension portion is identified, similar to identifying the path part at 206. The extension portion is, for example, a path segment, or an end point, of the desired extension. Optionally, instead of extending the suggested path, the user may indicate that she wants to truncate the path, before the end point of the suggested path. This may be done simply by indicating a point on the suggested path before its end. Optionally, the user specifically informs the software that the suggested path should be truncated rather than extended, for example by clicking on a menu choice.

The extension portion need not be limited to existing path parts that extend from the end of the active path. Optionally, the user can indicate a path segment or point not presently an extension of the active path, and a new path will be added to the set of paths, connecting that path segment or point to the end of the active path. The new connection between the indicated path segment or point, and the end of the active path, may be a straight line, or a more complicated algorithm may be used to generate the path.

Once the indication of the extension portion, or new end point, is received, a single new extension of the active path is suggested as the primary new path at 220, and the user is again given the opportunity to accept, completely reject, or partially reject it, at 210. Optionally the new suggested extension is displayed on the image in the same color as the active path, or in a different color. If there is a choice of paths to be suggested, then any of the criteria described above, for deciding which path to suggest at 208, may be used at 220 as well. The remarks in connection with 208 about optionally also suggesting other paths as secondary alternatives, or, in other embodiments of the invention, narrowing down the possible new paths to two or more possibilities for the user to choose between, apply to 220 as well.

It is expected that during the life of a patent maturing from this application many relevant segmentation algorithms will be developed and the scope of the term segmentation software is intended to include all such new technologies a priori. New intuitive input devices, replacing the mouse and the drop-down menu, may also be developed, and references to using a mouse and clicking are intended to include all such new technologies a priori.

As used herein the term "about" refers to ±10%.

The terms "comprises", "comprising", "includes", "including", "having" and their conjugates mean "including but not limited to". This term encompasses the terms "consisting of" and "consisting essentially of".

The phrase "consisting essentially of" means that the composition or method may include additional ingredients and/or steps, but only if the additional ingredients and/or steps do not materially alter the basic and novel characteristics of the claimed composition or method.

As used herein, the singular form "a", an and the include plural references unless the context clearly dictates otherwise. For example, the term "a compound" or "at least one compound" may include a plurality of compounds, including mixtures thereof.

The word "exemplary" is used herein to mean "serving as an example, instance or illustration". Any embodiment described as "exemplary" is not necessarily to be construed as preferred or advantageous over other embodiments and/or to exclude the incorporation of features from other embodiments.

The word "optionally" is used herein to mean "is provided in some embodiments and not provided in other embodiments". Any particular embodiment of the invention may include a plurality of "optional" features unless such features conflict.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

What is claimed is:

1. A method, performed by a computer, of facilitating selection by a user of one path from a set of directed paths in an image, comprising:
    a) generating the set of directed paths from a data representation comprising path segments in the image connected at their ends to other path segments, with each directed path in the set being an ordered sequence of connected path segments in the data representation, the different paths partly overlapping but the data representation not constituting a directed tree structure, each path beginning at a root and ending at an end point;
    b) receiving from the user an indication of a specified location in the image;
    c) identifying a specified path segment that best matches the indication of the specified location; and
    d) choosing a single path from among two or more paths belonging the set of directed paths, which two or more paths all include the specified path segment, but do not all follow a same route before the specified path segment, and at least one of which separates from another path somewhere along its length, and pointing out the chosen single path as a primary suggestion to the user.

2. A method according to claim 1, also comprising:
    a) receiving from the user an acceptance of the chosen path as the path to be selected, or a partial or complete rejection of the chosen path; and
    b) in response to a rejection received, choosing a single new path from the set of directed paths or from a changed set of directed paths, different from the previous suggested path, and pointing out the new path as a primary suggestion to the user.

3. A method according to claim 2, wherein receiving comprises receiving a complete rejection of the chosen path, and choosing the new path comprises choosing, in response to the rejection, a new path that includes a specified path segment that best matches a new indication of a specified location in the image, received from the user.

4. A method according to claim 2, wherein receiving comprises receiving a partial rejection of the chosen path, and choosing a new path comprises choosing a new path that, in response to the partial rejection, is chosen to include the same specified path segment as the previous chosen path.

5. A method according to claim 4, wherein the new path is chosen from a changed set of directed paths, and is not included in the original set of directed paths.

6. A method according to claim 4, wherein the new path is chosen, in response to the partial rejection, to be the same as the previous path from their root up to the specified path segment, differing from the previous path only after the specified path segment.

7. A method according to claim 6, also comprising receiving from the user an indication of an extension portion location in the image, wherein the new path is chosen to have a portion after the specified path segment, different from the previous path, that best matches the indicated extension portion location.

8. A method according to claim 2, also comprising receiving an indication from the user of a specified root, wherein choosing a path or choosing a new path, or both, comprises choosing a path beginning at the specified root.

9. A method according to claim 8, wherein choosing a path or choosing a new path, or both, comprises:
   a) evaluating a length of each of a plurality of paths from the specified root to the specified path segment; and
   b) giving priority to one or more paths that have shorter said length.

10. A method according to claim 2, wherein the image is a medical image, and the paths in the set of directed paths correspond to blood vessels in the image.

11. A method according to claim 10, wherein choosing a path, or choosing a new path, or both, comprises:
   a) for a plurality of paths, evaluating a degree to which the blood vessel corresponding to the path resembles a blood vessel in a category; and
   b) giving priority to one or more paths corresponding to blood vessels which have a greater degree of resemblance to vessels in said category.

12. A method according to claim 10, wherein choosing a path, or choosing a new path, or both, comprises giving higher priority to one or more paths that correspond to more major blood vessels.

13. A method according to claim 2, also comprising:
   a) receiving from the user an acceptance or a partial or complete rejection of at least one new suggested path, and in response to each partial or complete rejection received, choosing a single new path from the set of directed paths or from a changed set of directed paths, different from any of the previous suggested paths, and pointing out the new path as a primary suggestion to the user; and
   b) repeating the method of claim 2 and (a) at least once, to facilitate a selection by the user of one or more additional paths from the set of directed paths in the image, each time with previously selected paths excluded from the set of paths and from any changed set of directed paths.

14. A method according to claim 1, wherein the paths in the set of directed paths together include at least one loop.

15. A computer with access to image data, comprising:
   a) a monitor for displaying images from the image data;
   b) a user input device for indicating a location in the displayed image, and for receiving instructions from a user;
   c) a CPU programmed to perform the method of claim 1 to facilitate selection by the user of one path from a set of directed paths in the image, using the monitor and the input device to receive the indication of the specified location in the image, also programmed to run segmentation software for coronary arteries of a human heart; and
   d) a computer memory, configured to be used by the computer for storing instructions, data, or both, for performing the method of claim 1 for the network of coronary arteries in a human heart; wherein the CPU and the memory are capable to run the segmentation software and to perform the method of claim 1.

16. A computer according to claim 15, with no more than 4 gigabytes of memory.

17. A method, performed by a computer, of facilitating selection by a user of one path from a set of directed paths in an image, comprising:
   a) generating the set of directed paths from a data representation comprising path segments in the image connected at their ends to other path segments, with each directed path in the set being an ordered sequence of connected path segments in the data representation, the different paths partly overlapping, each path beginning at a root and ending at an end point;
   b) receiving from the user an indication of a specified location in the image;
   c) identifying a specified path segment that best matches the specified location;
   d) choosing a single path from among two or more paths belonging to the set of directed paths, which two or more paths all include the specified path segment, and pointing out the chosen single path as a primary suggestion to the user;
   e) receiving from the user a partial rejection of the chosen path, with an indication of an extension portion location in the image; and
   f) choosing a single new path in response to the partial rejection of the previous suggested path, from among paths in the set of directed paths or in a changed set of directed paths, having a portion after the specified path segment, different from the previous suggested path, that best matches the indication of the extension portion location, and pointing out the new path as a primary suggestion to the user.

18. A method according to claim 17, wherein the new path is chosen to have an end point that best matches the indication of the extension portion location.

19. A method according to claim 17, wherein the new path is chosen from among paths that are the same as the previous suggested path from the root to the specified path segment, but differs after the specified path part.

20. A method according to claim 17, wherein the new path is the same up to its end point as the previous chosen path, but ends before the previous chosen path ends.

21. A method according to claim 20, wherein the new path is so chosen in response to a request from the user to make the new path like the previous chosen path but truncated at an indicated end location.

22. A method according to claim 17, wherein the new path is chosen from a changed set of directed paths, and is not in the original set of directed paths.

23. A method according to claim 22, wherein at least a portion of the new path is not part of any path in the original set of directed paths.

24. A method of facilitating the selection by a user of a plurality of paths from a set of directed paths in an image, the method comprising, for each path to be selected:
   a) receiving from the user an indication of a specified location in the image;
   b) identifying a specified path segment that best matches the specified location;
   c) choosing a single path from among two or more paths belonging to the set of directed paths, which two or more paths all include the specified path segment, and pointing out the chosen single path as a primary suggestion to the user;
   d) receiving from the user an acceptance, a partial rejection, or a complete rejection of the chosen path, as the path to be selected;
   e) if a complete rejection is received, performing (a) through (c) again, and if a partial rejection is received, receiving from the user an indication of a new end location and choosing a single new path, in response to the partial rejection of the previous suggested path, from among paths belonging to the set of directed paths or to a changed set of directed paths, having a portion after the specified path segment, different from the previous suggested path, that best matches the indication of the extension portion location; and
   f) repeating (d) and (e) until an acceptance of the chosen path is received;
wherein a partial rejection is received for at least one chosen single path.

25. A method of facilitating the selection by a user of a plurality of paths from a set of directed paths in an image, the method comprising selecting one or more paths in the image by successively suggesting only one path at a time from the set of directed paths or from a changed set of directed paths, and each time receiving from the user an acceptance or a partial or complete rejection of each path as the path to be selected, until an acceptance is received, wherein previously selected paths are excluded from the set of directed paths and from any changed set of directed paths, and selecting at least one of the paths is done according to the method of claim 24.

26. A computer with access to image data, comprising:
   a) a monitor for displaying images from the image data;
   b) a user input device for indicating a location in the displayed image, and for receiving instructions from a user; and
   c) a CPU programmed to perform the method of claim 1 to facilitate selection by the user of one path from a set of directed paths in the image, using the monitor and the input device to receive the indication of the specified location in the image.

27. A computer with access to image data, comprising:
   a) a monitor for displaying images from the image data;
   b) a user input device for indicating a location in the displayed image, and for receiving instructions from a user;
   c) a CPU programmed to perform the method of claim 1 to facilitate selection by the user of one path from a set of directed paths in the image, using the monitor and the input device to receive the indication of the specified location in the image; and
   d) a computer memory, configured to be used by the computer for storing instructions, data, or both, for performing the method of claim 1 for the network of coronary arteries in a human heart.

28. A computer with access to image data, comprising:
   a) a monitor for displaying images from the image data;
   b) a user input device for indicating a location in the displayed image, and for receiving instructions from a user; and
   c) a CPU programmed to perform the method of claim 17 to facilitate selection by the user of one path from a set of directed paths in the image, using the monitor and the input device to receive the indication of the specified location in the image.

29. A computer with access to image data, comprising: a) a monitor for displaying images from the image data; b) a user input device for indicating a location in the displayed image, and for receiving instructions from a user; and c) a CPU programmed to perform the method of claim 17 to facilitate selection by the user of one path from a set of directed paths in the image, using the monitor and the input device to receive the indication of the specified location in the image, also programmed to run segmentation software for coronary arteries of a human heart; and d) a memory of no more than 4 gigabytes; wherein the CPU, and the memory are capable to run the segmentation software and to perform the method of claim 17 for the network of coronary arteries in a human heart.

* * * * *